United States Patent
Hirota et al.

(10) Patent No.: US 6,656,432 B1
(45) Date of Patent: Dec. 2, 2003

(54) MICROPIPETTE AND DIVIDEDLY INJECTABLE APPARATUS

(75) Inventors: Toshikazu Hirota, Kuwana (JP); Nobuo Takahashi, Owariasahi (JP); Yukihisa Takeuchi, Nishikamo-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/429,140

(22) Filed: Oct. 28, 1999

(30) Foreign Application Priority Data

Oct. 22, 1999 (JP) ............................................. 11-301627

(51) Int. Cl.[7] ................................................. G01N 3/02
(52) U.S. Cl. ........................... 422/100; 347/40; 347/68; 347/71; 422/63; 422/104
(58) Field of Search .................... 422/100, 99, 102, 422/104, 66, 63, 65; 347/68–72, 73–74, 87, 27, 40, 47, 54–55; 310/324, 330

(56) References Cited

U.S. PATENT DOCUMENTS

| | | | |
|---|---|---|---|
| 3,747,120 A | * | 7/1973 | Stemme |
| 4,216,483 A | | 8/1980 | Kyser et al. |
| 4,727,378 A | * | 2/1988 | Le et al. ........................ 347/21 |
| 4,730,197 A | * | 3/1988 | Raman et al. ................ 347/10 |
| 5,063,396 A | * | 11/1991 | Shiokawa et al. |
| 5,376,856 A | * | 12/1994 | Takeuchi et al. |
| 5,474,796 A | * | 12/1995 | Brennan |
| 5,475,279 A | * | 12/1995 | Takeuchi et al. ............ 310/328 |
| 5,689,291 A | * | 11/1997 | Tence et al. |
| 5,752,303 A | * | 5/1998 | Thiel |
| 5,877,580 A | | 3/1999 | Swierkowski |
| 5,916,524 A | | 6/1999 | Tisone |
| 5,958,342 A | | 9/1999 | Gamble et al. |
| 6,245,297 B1 | * | 6/2001 | Kowallis ..................... 422/100 |
| 6,277,334 B1 | * | 8/2001 | Ecker et al. |
| 6,284,113 B1 | * | 9/2001 | Bjornson et al. |

FOREIGN PATENT DOCUMENTS

| | | | |
|---|---|---|---|
| EP | 714022 A2 | * | 11/1995 |
| EP | 0 865 824 | | 9/1998 |
| JP | 6-40030 | | 2/1994 |
| JP | 6-40030 | * | 5/1994 |
| JP | 714022 A2 | * | 5/1996 |
| JP | 8-201265 | | 8/1996 |

OTHER PUBLICATIONS

Advanced Ceramics, Structural Ceramics, pp. 1–5 (Kirk–Othmer Encyclopedia of Chemical Technology, copywright 1991, John Wiley & Sons, Inc.).*

* cited by examiner

*Primary Examiner*—Joseph Drodge
(74) *Attorney, Agent, or Firm*—Burr & Brown

(57) ABSTRACT

A micropipette is provided including at least one substrate, an inlet port through which a sample is delivered from the outside, a cavity to be poured and filled with the sample, an introduction hole, and an injection port for expelling the sample are formed on the at least one substrate. The substrate for forming the cavity is made of ceramics, a piezoelectric/electrostrictive element is provided for at least one wall surface of the substrate, and the sample moves as a laminar flow in the cavity. The volume of the cavity is changed by driving the piezoelectric/electrostrictive element to expell al certain amount of the sample in the cavity from the injection port. According to the micropipette, it is possible to form microspots with high accuracy and high speed. According to a dispenser including the micropipette, it is possible to efficiently dispense hundreds to ten thousands of different samples at one time and form microspots. Therefore, productivity is remarkably improved.

8 Claims, 8 Drawing Sheets

MICROPIPETTE AND DIVIDEDLY INJECTABLE APPARATUS

BACKGROUND OF THE INVENTION AND RELATED ART STATEMENT

The present invention relates to a micropipette superior in droplet-volume controllability and productivity and preferably used to line and fix micro-volume droplets at a high density for applications such as manufacturing of DNA chips. The present invention further relates to a dispenser using micropipette.

The genetic-structure analyzing method has been remarkably advancing recently, and many genetic structures, including structures of human genes, have been clarified. To analyze the above genetic structures, a DNA chip is used in which thousands to tens of thousands or more of different types of DNA pieces are lined and fixed as microspots on a substrate, such as a microscope slide glass.

As methods for forming microspots in manufacturing the DNA chip, the QUILL method, the pin-and-ring method, and the spring pin method are widely used. Even when any method is used, it is necessary to decrease the fluctuation of volumes and shapes of microspots and keep the distance between microspots constant. Moreover, it is greatly desired that a new method exhibiting superior shape controllability and productivity of microspots is developed to further increase the density.

In this case, the QUILL method is a method for forming a microspot by storing samples in a concave portion formed at the tip of a pin, and making the pin tip contact a substrate, thereby moving the samples in the concave portion onto the substrate. However, there is a problem with respect to durability in that the pin tip is deformed or damaged due to the contact with a substrate, or a problem in that cross contamination easily occurs due to imperfect cleaning of the samples stored in the concave portion.

The pin and ring method is a method for forming spots on a substrate by reserving a sample solution in a microplate with a ring and thereafter catching the sample in the ring with the tip of a pin so that the solution passes through the ring. However, the number of types of samples that can be reserved at one time depends on the number of rings, which has been limited so far. Therefore, to form microspots of thousands to tens of thousands of types of samples, hundreds to thousands of cleaning and drying steps are also necessary. Thus, productivity is not as high as would be desired.

The spring pin method is a method for forming microspots by pressing a sample attached to the tip of a pin against a substrate, thereby moving the sample onto the substrate, in which pin and substrate damage are moderated by a double-pin structure having a built-in spring to spout the sample. However, only one-time spotting can be performed by one-time reservation. Therefore, the method is inferior in productivity.

Furthermore, with these conventional microspot-forming methods, because each sample solution is carried onto a substrate while it is exposed to the atmosphere, trouble occurs in that the sample is dried while it is carried and spotting cannot be performed. Therefore, a problem occurs in that a very expensive sample solution cannot be efficiently used.

Furthermore, a method for performing spotting by using the so-called ink-jet system practically used for a printer was studied. However, forming thousands to ten thousands of samples in separate channels has many problems from viewpoints of size and cost. Moreover, in case of the ink-jet system, it is necessary to fill a pump with samples without any bubbles before spotting. It is necessary to use much of the sample to fill the pump and, therefore, sample use efficiency is inferior. Furthermore, it is better for bubble discharge that a liquid moves through a channel including a pump chamber, at a high speed, thereby being agitated in the channel. Thus, when a delicate DNA solution is used as a sample, DNA may be damaged.

The present invention has been made to solve the above problems, and its object is to provide a micropipette making it possible to form microspots at a high accuracy and a high speed and to provide a dispenser having superior productivity using the micropipette which is capable of forming microspots by efficiently dispensing hundreds to tens of thousands of different samples at one time.

SUMMARY OF THE INVENTION

The present invention provides a micropipette comprising at least one substrate, an inlet port through which a sample is delivered from the outside, formed on the at least one substrate, a cavity into which the sample is poured and which is filled with the sample, and an injection port for expelling the sample formed on the at least one substrate. The substrate for forming the cavity is made of ceramics, at least one wall face of the substrate is provided with a piezoelectric/electrostrictive element, and the sample moves as a laminar flow in the cavity, wherein volumes of the cavity are changed by driving the piezoelectric/electrostrictive element, and a certain amount of the sample in the cavity is expelled from the injection port.

Because a micropipette of the present invention uses the above structure, a very small amount of a liquid is expelled through an injection port corresponding to each time a piezoelectric/electrostrictive element is driven and the volume of the liquid is very small and constant. The driving cycle can correspond to a high frequency by using the piezoelectric/electrostrictive element, and the time required for injection is also decreased. Moreover, because a sample moves in a closed space before the sample is expelled after it is delivered, the sample is not dried during that period. Furthermore, because the substrate can be compactly formed, it is possible to shorten the channel through which a sample moves and reduce the deterioration of use efficiency due to the attachment of the sample to the channel wall.

According to the present invention, it is preferable to previously fill a cavity with a displacement liquid, such as a buffer solution or physiologic saline solution, and then to deliver the sample into the cavity through the inlet port while laminar-flow-replacing the displacement liquid with the sample, and thereafter expel the sample in the cavity through an injection port by driving a piezoelectric/electrostrictive element. It is possible to control the completion of the laminar flow-replacing step, that is, the replacement time, by previously obtaining the velocity and the volume of the sample. However, it is more preferable to determine the end of the laminar flow-replacement by detecting the change of fluid characteristics in the cavity. Moreover, it is permitted to laminar-flow-replace a displacement liquid in the cavity with the sample from the inlet port while driving the piezoelectric/electrostrictive element. By previously securely replacing the inside of a cavity with an inexpensive replacement solution and then laminar-flow-replacing the inexpensive solution with an expensive sample, it is possible to completely prevent miss-injection from occurring and efficiently expel the expensive sample.

Moreover, according to the present invention, it is preferable to previously fill a cavity with a replacement solution such as a buffer solution or physiologic saline solution, and then to deliver a sample into the cavity through the inlet port while replacing the replacement solution with the sample, detect the end of the replacement by detecting the change of fluid characteristics in the cavity, and thereafter expel the sample in the cavity through an injection port by driving a piezoelectric/electrostrictive element. By detecting the change of fluid characteristics in the cavity and thereby determining the completion of replacement, it is possible to easily distinguish between the portion where the sample mixes with the replacement solution, and the portion where they do not mix with each other, and accurately clarify the portions even if they slightly mix in the channel. Therefore, it is possible to decrease the quantity of the sample mixed with the replacement solution that must be purged and improve the use efficiency of the sample.

Moreover, it is preferable to determine the change of fluid characteristics in the cavity by applying a voltage for exciting vibrations to the piezoelectric/electrostrictive element, and detecting the change of electric constants due to the vibrations. Thus, it is unnecessary to set a special detection element, and highly accurate yet inexpensive detection is realized.

According to the present invention, it is preferable that a sample inlet port, cavity, a sample injection port, and piezoelectric/electrostrictive element are formed at a plurality of places in one substrate. It is also preferred that a plurality of units, each of which includes a sample inlet port, a cavity, a sample injection port, and a piezoelectric/electrostrictive element formed in a substrate, and fixed to a fixing jig. Or, it is preferred to include three types of portions, such as a combination of a cavity and a piezoelectric/electrostrictive element, a sample inlet port, and a sample injection port are separately formed on at least two types of substrates and joined to each other. Alternatively, it is preferable to provide at least a cavity and a piezoelectric/electrostrictive element formed in the above substrate, and a unit formed by joining the above substrate or more, to one substrate on which one of either of a sample inlet port and a sample injection port are formed, and where the one unit, or more, are fixed and integrated.

Because each portion is formed at a plurality of places in one substrate, it is possible to compactly arrange the portions, form injection ports at a high accuracy and a high density, and expel a plurality of types of samples at the same time. By fixing a plurality of units, in each of which one portion is formed, in one substrate to constitute the whole, each substrate is easily manufactured and the yield is improved. Moreover, by joining at least two substrates, on each of which portions are formed as the whole, the range for selecting materials for the substrate is widened and it is possible to select an optimum material for each portion. Moreover, the yield of elements can be improved, the accuracy of the injection port can be improved, injection ports can be arranged at a high density, and a plurality of types of samples can be expelled at the same time.

Furthermore, it is preferable that the substrate is flat and injection ports of samples are formed on a side face or a major surface of the substrate, or that the substrate is flat, and injection ports of samples are formed on one of the opposing major surfaces of the substrate, and inlet ports of samples are formed on the other major surface of the substrate. By forming the substrate to be flat, the substrate can be manufactured by the green sheet lamination technique described later, and the whole becomes thin and compact. When injection ports are formed on a major surface of a substrate, it is possible to set the substrate in parallel with a flat plate on which injection ports are formed and easily keep the injection distance of droplets constant, and shapes of droplets are stabilized. Moreover, when injection ports are formed on the side face of a substrate, it is possible to longitudinally arrange flat substrates and thereby easily increase the density of the injection ports. Furthermore, by forming an inlet port and an injection port on opposite major surfaces, the length of the channel extending from the inlet port up to the injection port requires almost only the thickness of the flat plate, the channel of a sample solution is shortened and becomes simple, the frequency of the trouble that bubbles are caught in the channel to cause miss-injection can be decreased, and moreover, the sample use efficiency is improved.

Furthermore, it is permitted that two or more sample inlet ports are connected to one cavity. In case of this structure, it is possible to securely fill the cavity with samples by sucking or ejecting samples or a replacement solution through a plurality of inlet ports by adjusting the timing.

Furthermore, according to the present invention, it is preferable that a substrate in or on which a cavity and a piezoelectric/electrostrictive element are formed is made of zirconium ceramics, or that each substrate is made of zirconium ceramics. It is preferable that these substrates are manufactured by the green-sheet laminating and sintering method. Zirconia, is suitable and particularly stabilized zirconia and partially stabilized zirconia, because they have a large mechanical strength, a high toughness, a large durability to an acid/alkaline solution, and a small reactivity with piezoelectric films or electrode materials. Moreover, it is permitted that a substrate on which at least one inlet port and one injection port are formed is made of a metal or resin having superior formability characteristics and low cost.

Furthermore, a piezoelectric/electrostrictive film is preferably used for the piezoelectric/electrostrictive element because it is mainly made of lead zirconate, lead titanate, and lead magnesium niobate. Thereby, it has a high electromechanical coupling factor, a high piezoelectric constant, a small reactivity with the zirconia substrate when the piezoelectric film is sintered, and a stable composition.

Furthermore, the present invention provides a dispenser using a plurality of micropipettes respectively formed so that inlet ports through which a sample is delivered from the outside, cavities to be filled with the sample, and injection ports for expelling the sample are formed on at least one substrate. A piezoelectric/electrostrictive element is provided for at least one wall surface of the substrate for forming the cavities, and the sample moves as a laminar flow in the cavity, wherein the injection ports are vertically and horizontally lined and arranged, and different types of solution samples are injected from the injection ports.

Furthermore, the present invention provides a dispenser using a plurality of micropipettes respectively formed so that inlet ports through which a sample is delivered from the outside, a cavity into which the sample is poured and which is be filled with the sample, and injection ports for expelling the sample are formed on at least one substrate. The substrate forming the cavity is made of ceramics, and the substrate has a piezoelectric/electrostrictive element on at least one wall surface. The cavity is previously filled with a displacement solution, then the sample is poured into the cavity through the inlet ports while replacing a displacement solution with the sample. Completion of sample replacement in the cavity is determined by detecting the change of fluid characteristics in the cavity. Thereafter, the volume of the cavity is changed by driving the piezoelectric/electrostrictive element, and a certain amount of the sample in the cavity is expelled through the injection ports, which are vertically and horizontally lined and arranged, and different types of solution samples are expelled from the injection ports.

These dispensers make it possible to supply many types of samples at the same time by using a plurality of micropipettes and easily replace a locally-defective pipette with a new one. Moreover, because injection ports are vertically and horizontally lined and arranged, each of the above dispensers is preferably adopted when two-dimensionally lined and fixed microspots like a DNA chip are necessary.

It is preferable that each of these dispensers is provided with a mechanism in which cartridges separately filled with different types of solution samples are set to sample inlet ports to deliver different solution samples through inlet ports in order to improve the sample use efficiency. Moreover, it is preferable that each dispenser is provided with a mechanism in which a cartridge filled with a water-soluble solvent or organic solvent is set to each sample inlet port to clean the space from inlet ports up to injection ports formed in the substrate in order to expel thousands to tens of thousands of highly pure DNA pieces to very small spots without contamination.

Moreover, it is preferable that each of the dispensers has a different-directional-flying-droplet shielding plate made of a thin plate having a hole coaxial with an injection port outside the injection port. Thus, even if the expelling direction of an injection droplet is deviated, the droplet does not reach a substrate. Therefore, it is possible to prevent that the troubles of a spotting position being shifted or a spot mixing with an adjacent spot.

BRIEF DESCRIPTION OF THE DRAWINGS

FIG. 3(a) is a top view and FIG. 3(b) is a sectional view of FIG. 3(a) taken through the line A—A.

FIG. 4(a) is a top view, FIG. 4(b) is a side view, FIG. 4(c) is a top enlarged view of each unit, and FIG. 4(d) is a sectional view of FIG. 4(c).

FIG. 5(a) is a top view and FIG. 5(b) is a sectional view of FIG. 5(a) taken through the line B—B.

FIG. 6(a) is a top view and FIG. 6(b) is a sectional view of FIG. 6(a) taken through the line C—C.

FIG. 7(a) is a top view and FIG. 7(b) is a sectional view of FIG. 7(a) taken through the line D—D.

FIG. 8(a) is a top view and FIG. 8(b) is a sectional view of FIG. 8(a) taken through the line E—E.

FIG. 9(a) is a top view and FIG. 9(b) is a sectional view of FIG. 9(a) taken through the line F—F.

FIG. 11(a) is a top view and FIG. 11(b) is a sectional view of FIG. 11(a) taken through the line G—G.

DETAILED DESCRIPTION OF THE INVENTION

According to the basic structure of a micropipette of the present invention, a sample inlet port, a cavity to be filled with a sample, and a sample injection port are formed on at least one substrate, and a piezoelectric element is provided for at least one wall surface forming the cavity of the substrate. Moreover, the micropipette preferably has a structure that the sample moves as a laminar flow in the cavity. A micropipette having such a structure is able to efficiently form a microspot on a substrate or slide, such as a DNA chip, at a high accuracy and a high speed by changing volumes in a cavity in accordance with the driving of a piezoelectric/electrostrictive element and expelling a certain amount of a sample in the cavity through an injection port.

The present invention will be described below in detail in accordance with the embodiments shown in the accompanying drawings. However, the present invention is not restricted to the embodiments.

Figure 2:
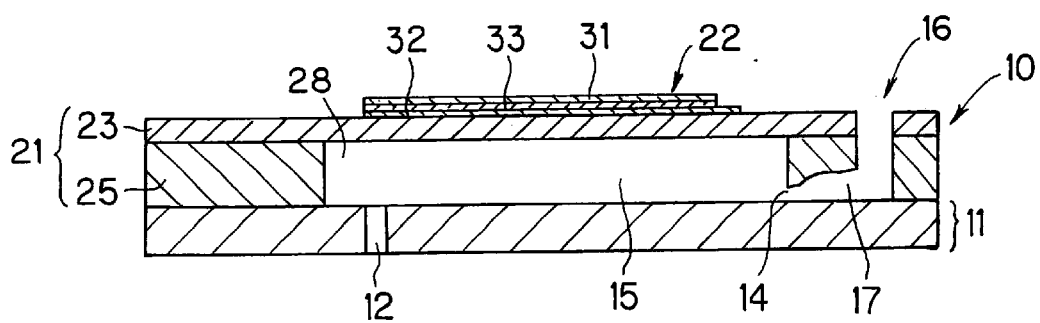
FIG. 2 is a sectional view showing a micropipette of the present invention.

FIG. 2 shows a micropipette of the present invention. In FIG. 2, a nozzle portion 11 is formed by forming a thin-wall flat nozzle plate 13 provided with an injection port 12 having at least one nozzle hole with a zirconia-ceramics green sheet, and a pump portion 21 is formed by forming a spacer plate 25 on which at least one chamber portion 28 is formed and a blocking plate 23 laminated on one side of the spacer plate 25 to cover the chamber portion 28 with a zirconia-ceramics green sheet respectively, and the whole is laminated and integrally sintered to constitute a substrate 10. Moreover, the blocking plate 23 is provided with a sample inlet port 16 and connected to an introduction hole 14 and a communication path 17 connected with the chamber portion 28 formed on the spacer plate 25.

Furthermore, a piezoelectric/electrostrictive element 22 having a lower electrode 31, a piezoelectric/electrostrictive layer 32, and an upper electrode 33 are formed on the outside face of the blocking plate 23.

According to the micropipette having the above structure, it is possible to manufacture a DNA chip lined and fixed as a microspot on a substrate such as microscope slide glass because, when an electric field is generated between the upper electrode 33 and the lower electrode 31, the piezoelectric/electrostrictive layer 32 is deformed, the volume of the cavity (pressuring chamber) 15 formed because the chamber portion 28 is covered, and thereby a sample solution containing DNA fragment filling the cavity 15 is expelled from the injection port 12 communicating with the cavity 15 at a predetermined speed. Moreover, as shown in FIG. 2, the structure of the so-called ink-jet system is disclosed in the specification of U.S. Pat. No. 5,933,170 and therefore, it is possible to refer to the specification.

In case of the micropipette having the above structure, a shape and dimensions of passage is formed to move solution sample containing DNA fragment as a laminar flow in the cavity (pressure chamber) 15.

Figure 1:
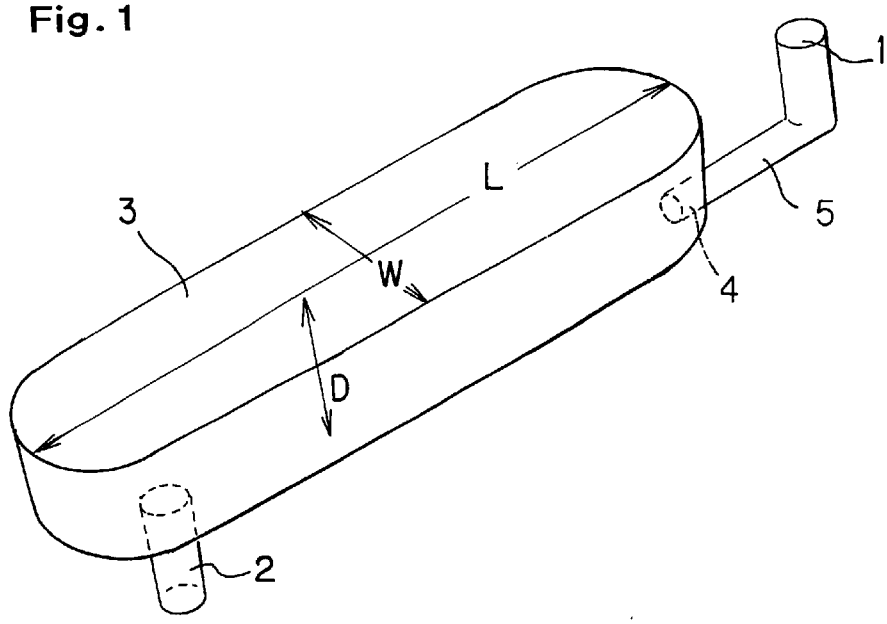
FIG. 1 is an illustration showing an example of a cavity.

A specific cavity will be described below by referring to FIG. 1. A cavity 3 is slender as shown in FIG. 1 and has a shape in which an inlet port 1 or an introduction port 4 for introducing a sample is formed at one end of the cavity 3 and an injection port 2 is connected to the other end of it. By forming the cavity 3 into the above shape, a sample moving into the cavity 3 from the inlet port 1 or through the communication path 5 and the introduction port 4 can be led to the injection port 2 without disturbing the flow of the sample by using the cavity 3 as a part of the passage extending from the inlet port 1 up to the injection port 2. Specific dimensions of the cavity 3 depend on the type of a sample, the size of a droplet to be formed, or the droplet forming density.

For example, in case of a micropipette for manufacturing a DNA chip requiring hundredths-of-micron-diameter droplet spotting of a sample obtained by dispersing sample liquid containing DAN fragment having 1 bp to 10,000 bp in a ×3SSC buffer solution {0.45M-sodium-chloride 0.045M-sodium-citrate aqueous solution (pH 7.0)} at a concentration of 1 μg/μl at hundredths-of-micron pitch, it is preferable to set a cavity length (L) to 1 to 5 mm, a cavity width (W) to 0.1 to 1 mm, and a cavity depth (D) to 0.1 to 0.5 mm. Moreover, it is preferable that the inner wall of the cavity is smooth so that there is no protrusion that disturbs a flow and that the cavity is made of ceramics having a high affinity for a sample solution.

Moreover, according to the present invention, it is preferable to pre-fill a cavity with a buffer solution or physiological saline solution, then pour a sample into the cavity through an inlet port while laminar-flow-replacing with the sample, and thereafter drive a piezoelectric/electrostrictive element. Moreover, in this case, it is preferable to determine the completion of laminar flow replacement of the sample in the cavity by detecting the change of fluid characteristics in the cavity. Furthermore, it is preferable that the replacement of the sample with a displacement liquid is carried out in the form of a laminar flow.

However, when characteristics of samples are changed, or the solution velocity is very high, or in case where the inside of the cavity nearby an introduction hole, it is not always necessary to use a laminar flow. In this case, though the amount of the sample to be purged increases due to mixing of the sample with the displacement liquid, it is possible to minimize the increase of the amount of the sample to be purged by detecting the change of fluid characteristics in the cavity and thereby judging the completion of replacement. In this case, the change of fluid characteristics in the cavity is determined by applying a voltage for exciting vibrations to the piezoelectric/electrostrictive element and detecting the change of electric constants due to the vibrations. The above detection of the change of fluid characteristics is disclosed in the specification of U.S. Pat. No. 5,889,351 and therefore, it is possible to refer to the contents of the specification.

Specifically, the electrical connection from a driving power supply is disconnected from an optional piezoelectric/electrostrictive element by a relay at a predetermined interval and simultaneously, the means for measuring a resonance frequency is connected by the relay to electrically measure the impedance or resonation frequency at that point of time. Thereby, it is possible to determine whether the viscosity and specific gravity of a solution is equal to those of a purposed sample (solution containing DNA fragment and the like). That is, in the case of a micropipette of the present invention, it is possible to simplify the structure of the micropipette because the micropipette functions as a sensor. Accordingly, a displacement liquid, such as a buffer solution or physiological saline solution, can be poured through an inlet port into the cavity while expelling the sample. Similarly, the sample remaining in the cavity can be completely discharged through laminar-flow replacement, and the next sample injection can be prepared. In this case, detecting whether a sample remains in the cavity (whether the sample can be expelled as a sample) can be also determined by detecting the change of fluid characteristics in the cavity. Thus, by using a micropipette of the present invention, it is possible to greatly decrease the amount of unused sample wasted through laminar-flow replacement or by a replacement-completion detecting mechanism, and thus improve the sample use efficiency.

Figure 3A:
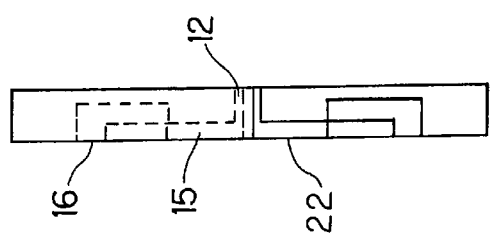
FIGS. 3(a) and 3(b) show another type of a micropipette of the present invention.
Figure 3B:
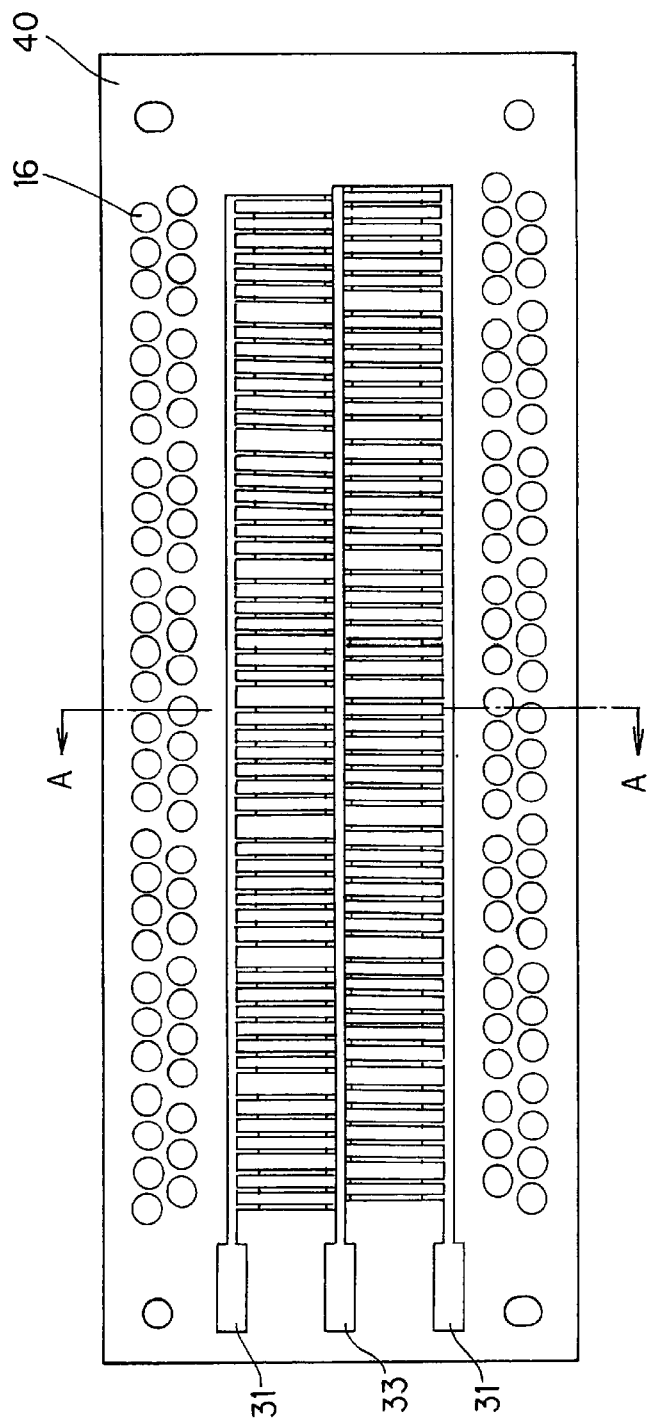

FIGS. 3(a) and 3(b) to FIGS. 9(a) and 9(b) show other types of micropipettes of the present invention. In FIGS. 3(a) and 3(b), pluralities of sample inlet ports 16, cavities 15, sample injection ports 12, and piezoelectric/electrostrictive elements 22 are formed in/on one substrate 40 and the upper electrode 33 and lower electrode 31 of each piezoelectric/electrostrictive element 22 are collectively extended outward. This is preferable because it is possible to expel different types of samples at the same time and efficiently manufacture DNA chips at a high productivity.

Figure 4A:
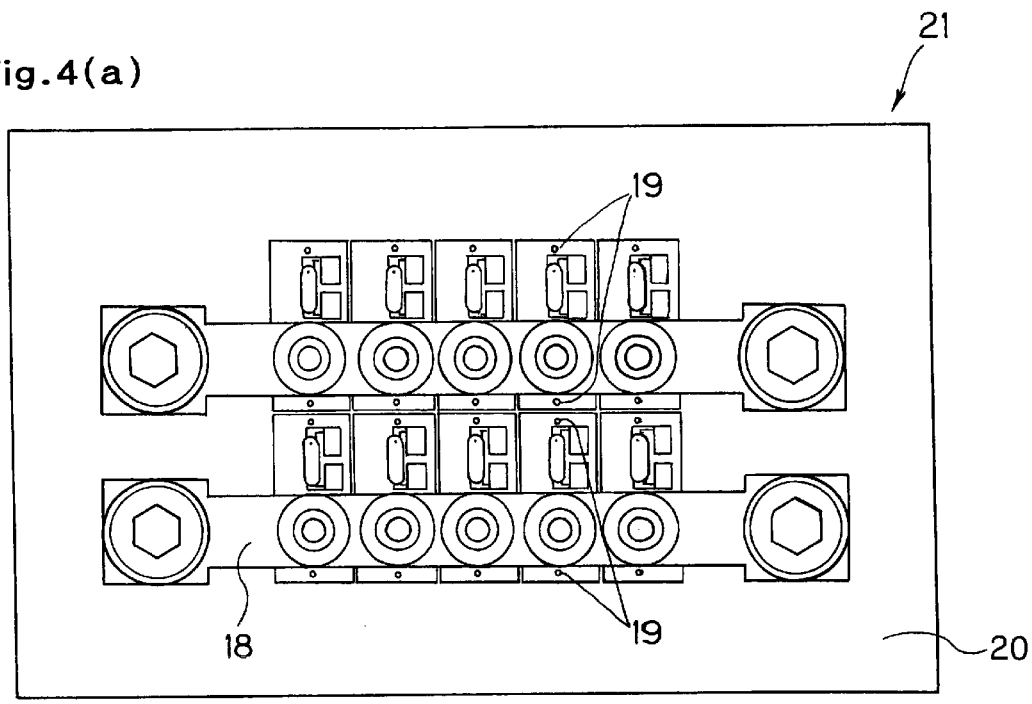
FIGS. 4(a), 4(b), 4(c), and 4(d) show still another type of a micropipette of the present invention.
Figure 4B:
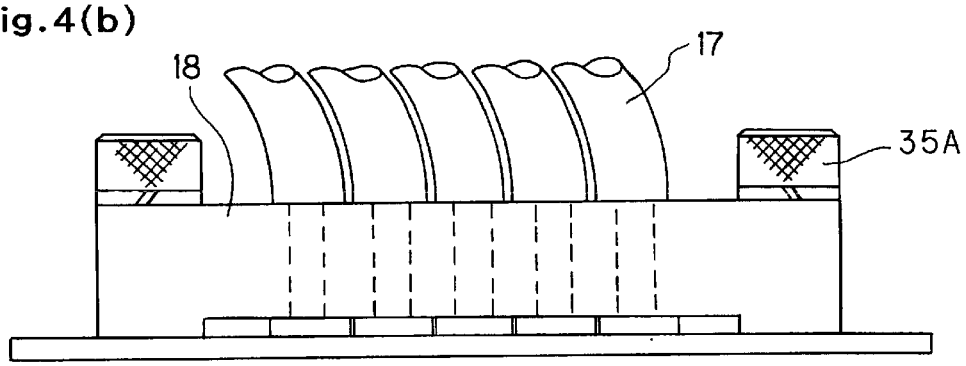
Figures 4C, 4D:
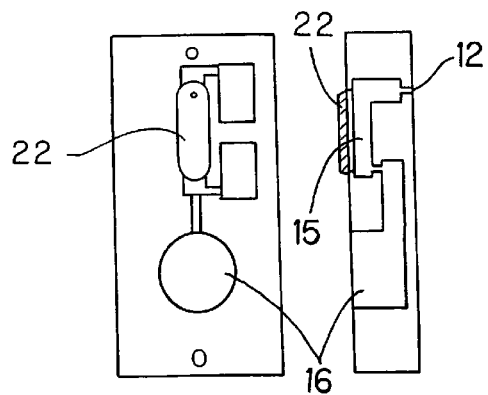

The micropipette in FIGS. 4(a) and 4(b) shows an embodiment formed by fixing a plurality of units in each of which one sample inlet port 16, one cavity 15, sample injection port 12, and one piezoelectric/electrostrictive element 22 are formed in one substrate (see FIGS. 4(c) and 4(d)) to a fixing jig 35 (i.e., a general name for a pressing jig 18, positioning pin 19, and fixing plate 21). Each unit is fixed to the fixing plate 21, by the positioning pin 19 and the pressing jig 18 for holding a tube 17 (communication path) for supplying a sample to the sample inlet port 16. Though each unit is fixed by fastening both ends of the pressing jig 18 to the fixing plate 20 by a screw 35A in FIGS. 4(a) and 4(b), it is also possible to mechanically fix each unit by a screw and a spring or fix each unit by an adhesive.

A substrate 40 on which the sample inlet port 16, cavity 15, and sample injection port 12 are formed shown in FIGS. 3(a) and 3(b) and FIGS. 4(a) to 4(d) is made of ceramics. Moreover, one of stabilized zirconia, partially stabilized zirconia, alumina, magnesia, and silicon nitride can be used. Among these materials, stabilized or partially stabilized zirconia is most preferably used because it has a large mechanical strength, a high toughness, and a small reactivity with piezoelectric films or electrode materials even in the form of a thin plate. Moreover, when stabilized or partially stabilized zirconia is used as the material of the substrate 40, it is preferable that a portion on which the piezoelectric/electrostrictive element 22 is formed contains an additive such as alumina or titania.

Moreover, the piezoelectric/electrostrictive layer of the piezoelectric/electrostrictive element 22 can use composite ceramics containing the component of one of lead zirconate, lead titanate, lead magnesium niobate, lead magnesium tantalate, lead nickel niobate, lead zinc niobate, lead manganese niobate, lead antimony stannate, lead manganese tungstate, lead cobalt niobate, and barium titanate or a combination of any of the above substances. In the case of the present invention, a material mainly containing lead zirconate, lead titanate, and lead magnesium niobate is preferably used. This is because the above material has not only a high electromechanical coupling factor and a high piezoelectric constant but also a small reactivity with a substrate material when a piezoelectric film is sintered and thereby, makes it possible to stably form an object having a predetermined composition.

Moreover, it is permitted to use ceramics which contain oxides or the like of the following substances as an independent substance, or a mixture in addition to the above piezoelectric ceramics: lanthanum, calcium, strontium, molybdenum, tungsten, barium, niobium, zinc, nickel, manganese, cerium, cadmium, chromium, cobalt, antimony, iron, yttrium, tantalum, lithium, bismuth, and tin or the like. For example, it is preferable to use ceramics mainly consisting of lead zirconate, lead titanate, and lead magnesium niobate and moreover, containing lanthanum and/or strontium.

It is preferable that the upper electrode and the lower electrode of a piezoelectric/electrostrictive element are solid at room temperature and consist of a conductive metal. For example, it is permitted to use a metal alone, such as aluminum, titanium, chromium, iron, cobalt, nickel, copper, zinc, niobium, molybdenum, ruthenium, palladium, rhodium, silver, tin, tantalum, tungsten, iridium, platinum, gold, and lead, or an alloy obtained by combining any ones of these metals. Moreover, a cermet material obtained by dispersing the same material as that of the piezoelectric film in any of the above metals can be used. A substrate, piezoelectric/electrostrictive element, and electrode made of any one of the above materials are used for all embodiments of the present invention in common.

Figure 5A:
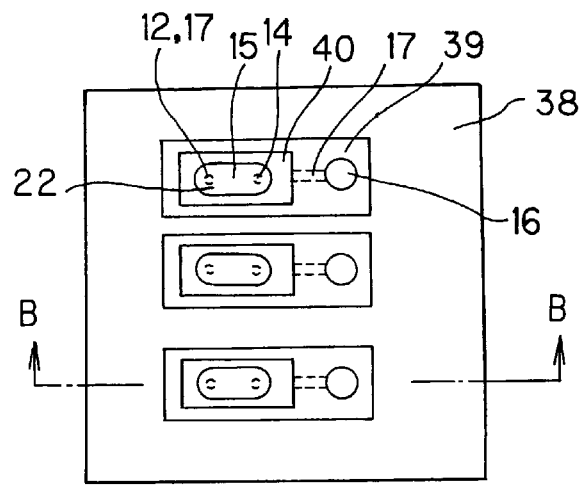
FIGS. 5(a) and 5(b) show still another type of a micropipette of the present invention.
Figure 5B:
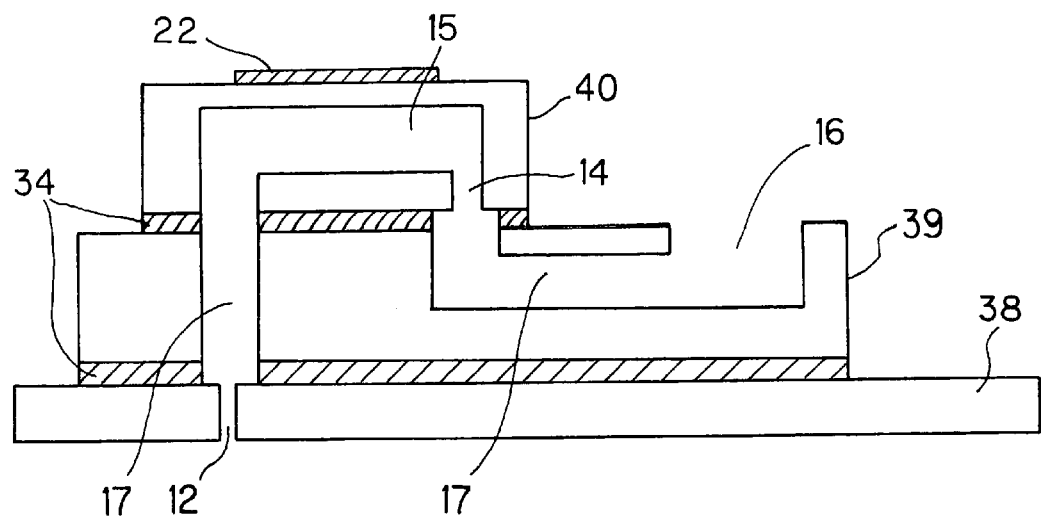

FIGS. 5(a) and 5(b) show an embodiment of a micropipette composed of a substrate 40 having a cavity 15, a piezoelectric/electrostrictive element 22, and an introduction hole 14, a substrate 39 having a set of one inlet port 16 and two communication paths 17, and a substrate 38 having a plurality of injection ports 12, the substrates 40, 39, and 38 being joined into one body by an adhesive 34. The substrate 40 is made of partially stabilized zirconia, the substrate 39 is made of stainless steel, and the substrate 38 is made of polyimide resin. Though it is permitted to mechanically join the substrates each other, it is preferable to join them by an adhesive or through thermal diffusion in order to keep the channel sealing characteristic.

The adhesive used is properly selected from the viewpoints of the combination of substrate material and thermal expansion coefficient and stability against sample-solution. It is suitable to use one of vinyl-, acrylic-, phenol-, polyamide-, resorcinol-, urea-, melanin-, polyester-, epoxy-, furan-, polyurethane-, silicon-, rubber-, polyimide-, and polyolefin-based adhesives. Particularly, epoxy- and polyimide-based adhesives are preferable from the viewpoints of adhesive strength and durability. Moreover, it is possible to use each adhesive mixed with very small beads made of glass or the like in order to keep the thickness of the adhesive constant.

Figure 6A:
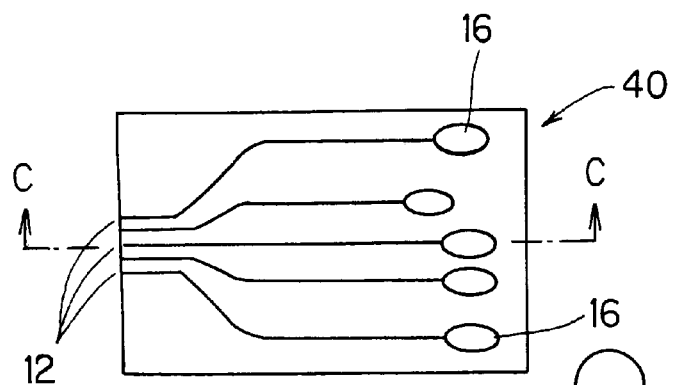
FIGS. 6(a) and 6(b) show still another type of a micropipette of the present invention.
Figure 6B:
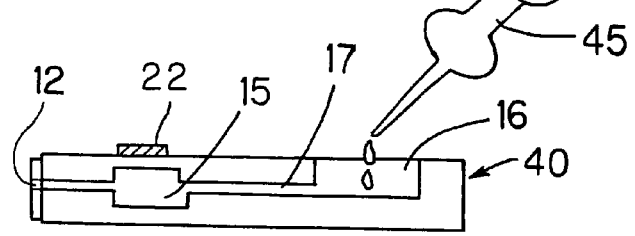

FIGS. 6(a) and 6(b) show another embodiment of a micropipette of the present invention. This micropipette is referred to as the so-called edge type, in which a sample inlet port 16, a cavity 15, a sample injection port 12, and a piezoelectric/electrostrictive element 22 are formed at a plurality of places in/on one substrate 40. Moreover, in the case of this micropipette, the sample injection port 12 is formed on the side face of the substrate 40 and a sample delivered into the sample inlet port 16 from a normal micropipette 45 passes through a communication path 17 in the substrate 40, and enters and fills the cavity 15. The micropipette changes the volume in the cavity 15 by driving the piezoelectric/electrostrictive element 22 to expel a certain amount of the sample filling the cavity 15 through the injection port 12.

Figure 7A:
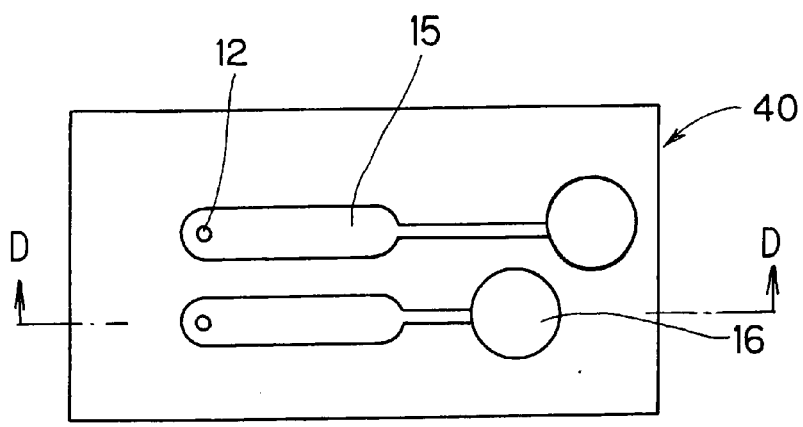
FIGS. 7(a) and 7(b) show still another type of a micropipette of the present invention.
Figure 7B:
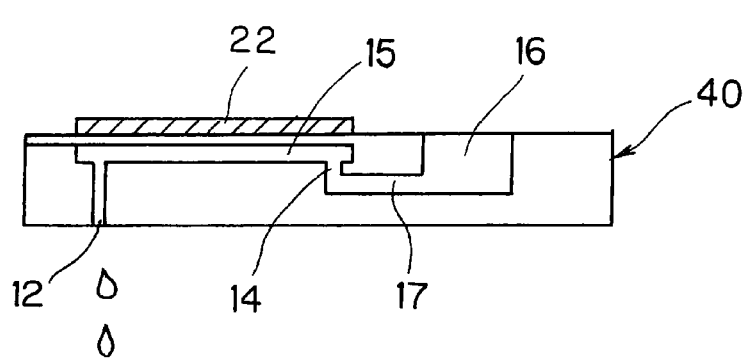

FIGS. 7(a) and 7(b) show still another embodiment of a micropipette of the present invention. This micropipette is referred to as the so-called face type same as those shown in FIGS. 3(a) and 3(b) to FIGS. 5(a) and 5(b), in which a sample inlet port 16, a cavity 15, a sample injection port 12, and a piezoelectric/electrostrictive element 22 are formed at a plurality of places in/on one substrate 40 similarly to the case of FIGS. 6(a) and 6(b). Moreover, in case of this micropipette, the sample injection port 12 is formed on a major surface of the substrate 40. The cavity 15 and the sample inlet port 16 are connected by an introduction hole 14 and a communication path 17.

Figure 8A:
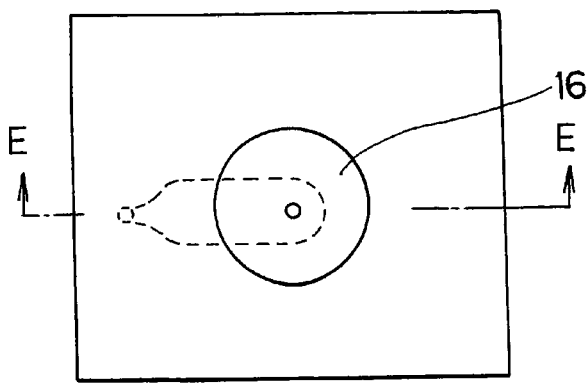
FIGS. 8(a) and 8(b) show still another type of a micropipette of the present invention.
Figure 8B:
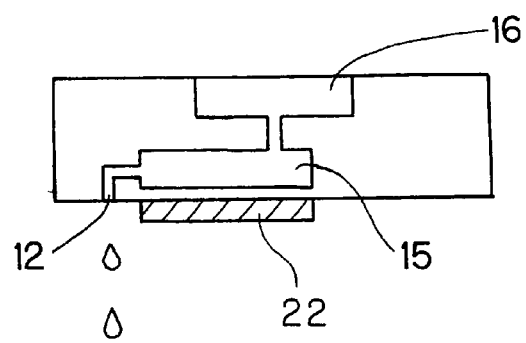

FIGS. 8(a) and 8(b) show an embodiment in which a substrate 40 is formed into a flat plate, a sample injection port 12 is formed on one of the opposing major surfaces of the substrate, and a sample inlet port 16 is formed on the other major surface of the substrate. The piezoelectric/electrostrictive element 22 is formed on the same major surface as the injection port.

Figure 9A:
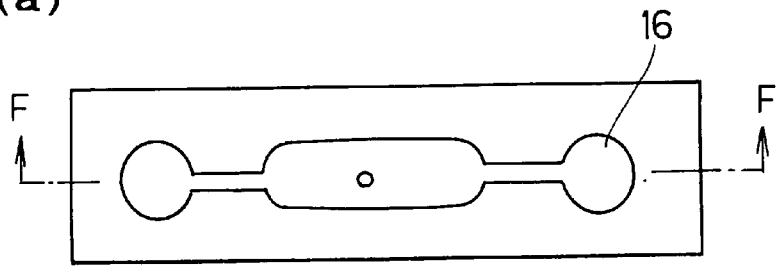
FIGS. 9(a) and 9(b) show still another type of a micropipette of the present invention.
Figure 9B:
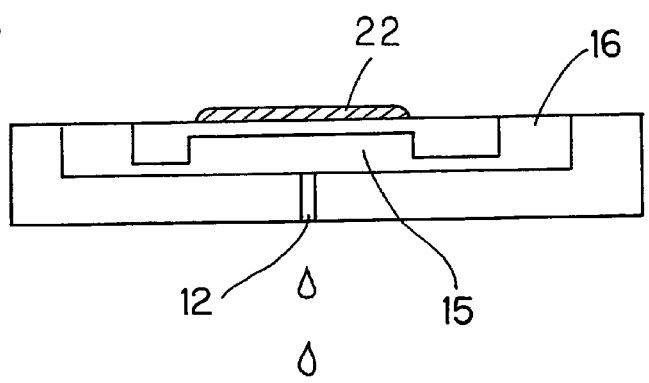

FIGS. 9(a) and 9(b) show an embodiment in which two sample inlet ports 16 are connected to one cavity 15. A piezoelectric/electrostrictive element 22 is formed on the same major surface as the sample inlet ports 16, and a sample injection port 12 is formed on the other major surface.

Figure 10:
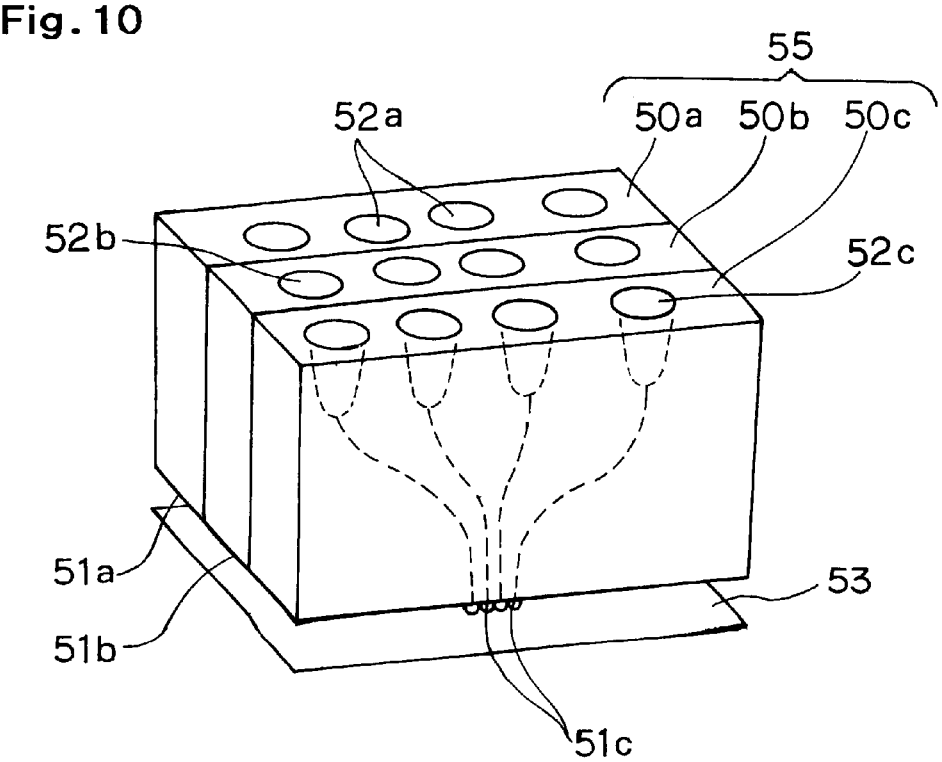
FIG. 10 is a perspective view showing a dispenser.
Figure 11A:
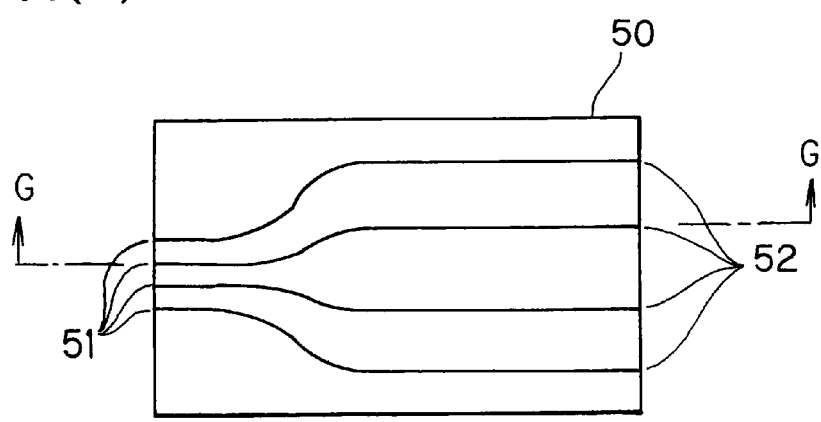
FIGS. 11(a) and 11(b) show the micropipette used for the dispenser in FIG. 10.
Figure 11B:
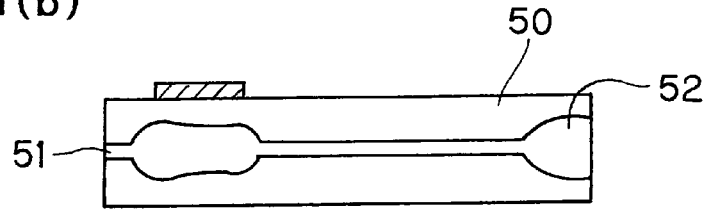

Next, a dispenser using one of the above micropipettes will be described. FIG. 10 shows a dispenser 55 formed by vertically setting a plurality of micropipettes 50 (50a, 50b, and 50c), respectively, having a sample inlet port 52 and sample injection port 51 as shown in FIGS. 11(a) and 11(b) while turning the sample injection ports downward. That is, the micropipettes 50a, 50b, and 50c are formed so that sample inlet ports 52a, 52b, and 52c are turned upward, sample injection ports 51a, 51b, and 51c are turned downward and are vertically and horizontally lined and arranged. Different types of solution samples are expelled through the sample injection ports 51a, 51b, and 51c. A different-directional-flying shielding plate 53, made of a thin plate having a hole coaxial with an injection port, is set further below the sample injection ports 51a, 51b, and 51c.

Figure 12:
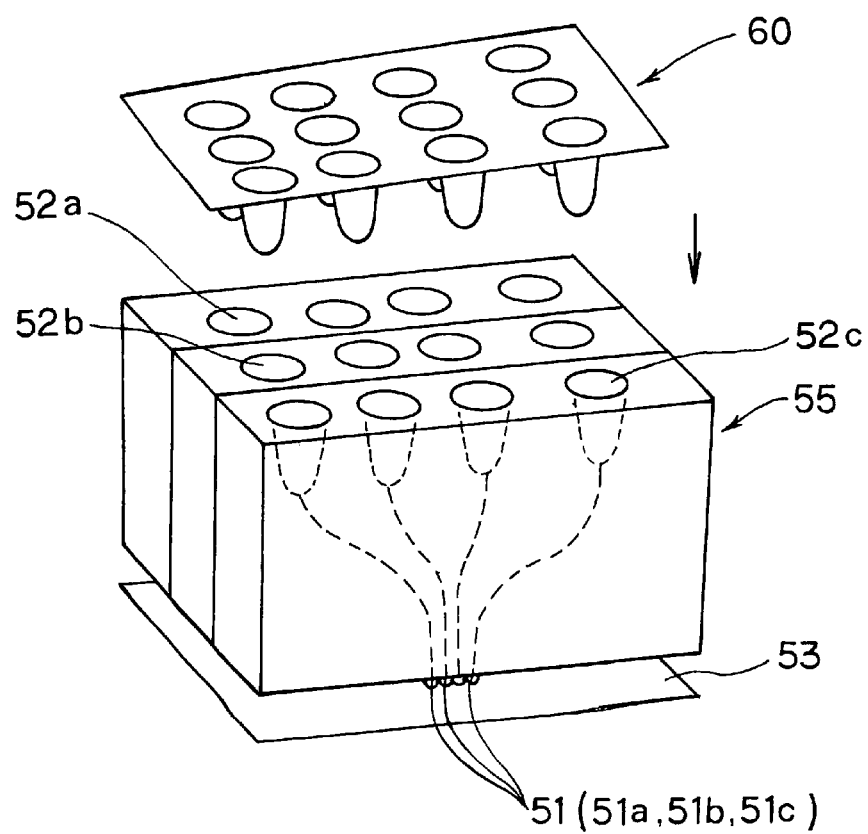
FIG. 12 is a perspective view showing a state of setting a cartridge to a dispenser.

It is preferable that the dispenser 55 having the above structure is provided with a mechanism in which a cartridge 60 whose holes are filled with different types of solution samples, is set to the sample inlet ports 52a, 52b, and 52c one to one to expel different solution samples through the discharge ports 51a, 51b, and 51c as shown in FIG. 12. With this arrangement, samples can be efficiently expelled. Moreover, it is preferable that the dispenser 55 is provided with a mechanism in which a cartridge filled with a physiological saline solution or organic solvent set to each sample inlet port to clean the space formed in the substrate extending from inlet ports up to injection ports in order to expel thousands to ten thousands of DNA fragments to very small spots without contamination and at a high purity. To deliver a sample or the like into each sample inlet port from a cartridge, it is also permitted to set a cartridge to an inlet port and then open the bottom of the cartridge with a needle or the like, or to use a method of previously forming a needle or the like near an inlet port so that the cartridge is opened at the same time the cartridge is set. Moreover, it is permitted to add a mechanism for forcibly feeding gas or the like after opening the cartridge and forcibly pushing out the sample or the like.

Next, a DNA-chip manufacturing method using the dispenser 55 of the present invention will be described below.

In general, a sample containing DNA fragments to be spotted for a DNA chip is used by amplifying the DNA fragments in the cartridge 60, as shown in FIG. 12. However, in case of a dispenser of the present invention using a micropipette having a slight space in a substrate, it is permitted to perform amplification in the micropipette.

When the DNA fragments are amplified in the cartridge 60, the cartridge filled with a buffer solution serving as displacement liquid is previously set and then the cavity of each micropipette is filled with the buffer solution. The cartridge filled with a DNA-fragment sample is set to an inlet port, and the bottom of the cartridge is opened by a needle or the like to deliver the sample into the inlet port. Thereafter, the buffer solution in the cavity is laminar-flow-replaced with the sample, expelling the previously-poured buffer solution through the injection port by driving a piezoelectric/electrostrictive element.

A replacement completion point is detected by making the piezoelectric/electrostrictive element function as a sensor to detect the viscosity and specific gravity of the solution in the cavity by switching a relay. After the replacement is complete, a DNA chip is manufactured by driving the piezoelectric/electrostrictive element in accordance with an element driving condition suitable for the number of droplets corresponding to a required spot diameter and repeating spotting. In general, one spot is formed by expelling one droplet to hundreds of droplets from a micropipette. When the amount of the sample in an inlet port is decreased, it is possible to completely use the sample without leaving the sample in the micropipette by adding a buffer solution and continuing to expel the sample so that bubbles do not enter a channel. Completion of the replacement of the sample with the displacement liquid (completion of sample expelling) is performed by similarly detecting the viscosity and specific gravity of the solution with the piezoelectric/electrostrictive element. Moreover, it is preferable to use a sample solution whose concentration is previously lowered, and to dry the solvent while forming microspots on a substrate. By using this method, it is possible to further reduce the amount of the sample remaining in a channel and improve the sample use efficiency.

Furthermore, it is preferable to use a displacement liquid and sample from which a dissolved gas is previously removed through deaeration. By using such a deaerated solution, it is possible to avoid the trouble of bubbles being caught in the channel and thereby preventing the channel from being filled with solution (because bubbles are dissolved in the solution) when filling the channel with the solution, and preventing expelling trouble when bubbles are produced in the fluid while the fluid is expelled.

As described above, a micropipette of the present invention makes it possible to form microspots at a high accuracy and a high speed.

Moreover, a dispenser using the micropipette makes it possible to form microspots by efficiently dispensing hundreds to ten thousands of different samples at one time and thus, the productivity is remarkably improved.

What is claimed is:

1. A dispenser comprising:

a plurality of micropipettes, each of said micropipettes comprising an inlet port through which a sample solution is delivered from the outside, a cavity into which the sample solution is poured and which is filled with the sample solution, and an injection port for expelling the sample solution in communication with said cavity, said inlet port, said cavity and said injection port being formed in or on at least one substrate, and a piezoelectric/electrostrictive element provided on at least one wall surface of the substrate that forms said cavity, wherein said injection ports are vertically and horizontally aligned and arranged with one another, and a mechanism including a plurality of cartridges filled with different types of sample solutions, each cartridge being connected to the inlet port of each respective micropipette so as to deliver a different sample solution to each respective micropipette.

2. A dispenser comprising:

a plurality of micropipettes, each of said micropipettes comprising an inlet port through which a sample solution is delivered from the outside, a cavity into which the sample solution is poured and which is filled with the sample solution, and an injection port for expelling the sample solution in communication with said cavity, said inlet port, said cavity and said injection port being formed in or on at least one substrate, and a piezoelectric/electrostrictive element provided on at least one wall surface of the substrate that forms said cavity, wherein said injection ports are vertically and horizontally aligned and arranged with one another; and a thin plate having a hole that is coaxial with the central axis of each of said injection ports, said thin plate being provided on the outside of each of said injection ports.

3. A dispenser comprising:

a plurality of micropipettes, each of said micropipettes comprising an inlet port through which a sample solution is delivered from the outside, a cavity into which the sample solution is poured and which is filled with the sample solution, and an injection port for expelling the sample solution in communication with said cavity, said inlet port, said cavity and said injection port being formed in or on at least one substrate, and a piezoelectric/electrostrictive element provided on at least one wall surface of the substrate that forms said cavity, wherein said injection ports are vertically and horizontally aligned and arranged with one another;

a mechanism including a plurality of ridges filled with a water-soluble solvent or an organic solvent, each cartridge being connected to the inlet port of each respective micropipette so as to clean a space extending from said inlet port up to said injection port of each micropipette.

4. The dispenser according to claim 3, further comprising a thin plate having a hole that is coaxial with the central axis of each of said injection ports, said thin plate being provided on the outside of each of said injection ports.

5. A dispenser comprising:

a plurality of micropipettes, each of said micropipettes comprising an inlet port through which a sample solution is delivered from the outside, a cavity into which the sample solution is poured and which is filled with the sample solution, and an injection port for expelling the sample solution formed in communication with said cavity, said cavity, said inlet port and said injection port being formed in or on at least one substrate, and a piezoelectric/electrostrictive element provided on at least one wall surface of the substrate that forms said cavity, wherein said injection ports are vertically and horizontally aligned and arranged with one another;

a mechanism including a plurality of cartridges filled with different types of sample solutions, each cartridge being connected to the inlet port of each respective micropipette so as to deliver a different sample solution to each respective micropipette;

wherein said cavity of each micropipette is first filled with a displacement solution, then a sample solution is poured into said cavity through said inlet port while replacing the displacement solution with the sample solution, completion of sample solution replacement in the cavity is determined by detecting a change of fluid characteristics of the fluid in said cavity, and thereafter a volume of said cavity is changed by driving said piezoelectric/electrostrictive element and a certain amount of different sample solution is expelled trough said injection ports of each respective micropipette.

6. The dispenser according to claim 5, further comprising a thin plate having a hole that is coaxial with the central axis of each of said injection ports, said thin plate being provided on the outside of each of said injection ports.

7. A dispenser comprising:

a plurality of micropipettes, each of said micropipettes comprising an inlet port through which a sample solution is delivered from the outside, a cavity into which the sample solution is poured and which is filled with the sample solution, and an injection port for expelling the sample solution formed in communication with said cavity, said cavity, said inlet port and said injection port being formed in or on at least one substrate, and a piezoelectric/electrostrictive element provided on at least one wall surface of the substrate that forms said cavity, wherein said injection ports are vertically and horizontally aligned and arranged with one another;

a mechanism including a plurality of cartridges filled with a water-soluble solvent or an organic solvent, each cartridge being connected to the inlet port of each respective micropipette so as to clean a space extending from said inlet port up to said injection port of each micropipette;

wherein said cavity of each micropipette is first filled with a displacement solution, then a sample solution is poured into said cavity through said inlet port while replacing the displacement solution with the sample solution, completion of sample solution replacement in the cavity is determined by detecting a change of fluid characteristics of the fluid in said cavity, and thereafter a volume of said cavity is changed by driving said piezoelectric/electrostrictive element and a certain amount of sample solution is expelled through said injection port of each respective micropipette.

8. The dispenser according to claim 7, further comprising a thin plate having a hole that is coaxial with the central axis of each of said injection ports, said thin plate being provided on the outside of each of said injection ports.

* * * * *